United States Patent
Kuo

(10) Patent No.: US 6,386,864 B1
(45) Date of Patent: May 14, 2002

(54) STRESS INDICATORS FOR TOOTH POSITIONING APPLIANCES

(75) Inventor: Eric Kuo, Sunnyvale, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

(21) Appl. No.: 09/608,593

(22) Filed: Jun. 30, 2000

(51) Int. Cl.$^7$ ................................................ A61C 3/00

(52) U.S. Cl. ................................................ 433/6; 433/215

(58) Field of Search ................................ 433/6, 215

(56) References Cited

U.S. PATENT DOCUMENTS

| | | | |
|---|---|---|---|
| 4,324,547 A | * | 4/1982 | Arcan et al. .................. 433/71 |
| 4,500,294 A | * | 2/1985 | Lewis ........................ 433/215 |
| 5,975,893 A | | 11/1999 | Chishti et al. .................. 433/6 |

FOREIGN PATENT DOCUMENTS

WO    WO 98/58596    12/1998

* cited by examiner

*Primary Examiner*—John J. Wilson
(74) *Attorney, Agent, or Firm*—Townsend and Townsend and Crew LLP; Bao Tran

(57) ABSTRACT

The present invention provides dental appliances, systems and methods which allow orthodontic practitioners to more easily monitor patient treatment progress. When using elastic repositioning appliances in orthodontic treatment, a patient may wear such an appliance until their teeth have repositioned to the tooth configuration prescribed by the appliance. At that point, the patient should progress to the next appliance for repositioning to the next tooth configuration in the treatment plan. Indications that the appliance is no longer supplying significant repositioning forces may be beneficial in the determination of progressing the patient to the next appliance or next stage in treatment. Mechanical stress in the material of the appliance, when the appliance is in place over the patient's teeth, may serve as an indicator of repositioning force applied against the teeth. Such stress may be visualized with the use of photoelastic material in or on the appliance.

17 Claims, 2 Drawing Sheets

STRESS INDICATORS FOR TOOTH POSITIONING APPLIANCES

BACKGROUND OF THE INVENTION

The present invention is related generally to the field of orthodontics. Particularly, the present invention is related to a dental appliance for repositioning teeth and a method of determining the useful life of such an appliance for this purpose.

Orthodontic treatments involve repositioning misaligned teeth and improving bite configurations for improved cosmetic appearance and dental function. Repositioning is accomplished by applying gentle controlled forces to the teeth over an extended period of time. Due to the limited space within the oral cavity and extensive movements that some teeth must undergo, the teeth will often be moved throughout a series of intermediate patterns to properly arrange the teeth. For example, molars may be temporarily moved backwards (distalized) to create adequate space for movement of the incisors. Thus, a single patient may experience an average of 25–30 stages or alignment patterns before achieving the final desired configuration.

Recently, it has been found that such repositioning may be accomplished with the use of a series of removable elastic positioning appliances. Such appliances comprise a thin shell of elastic material that generally conforms to a patient's teeth but is slightly out of alignment with an initial or immediately prior tooth configuration. Placement of the elastic positioner over the teeth applies controlled forces in specific locations to gradually move the teeth into the new configuration. Repetition of this process with successive appliances comprising new configurations eventually move the teeth through a series of intermediate configurations or alignment patterns to a final desired configuration. A full description of an exemplary elastic polymeric positioning appliance is described in U.S. Pat. No. 5,975,893, and in published PCT application WO 98/58596 which designates the United States and which is assigned to the assignee of the present application. Both these documents are incorporated by reference for all purposes.

A patient generally uses a repositioning appliance, corresponding to a given stage in a treatment plan, until the appliance is no longer applying sufficient repositioning forces to the patient's teeth. When a patient first places an appliance over their teeth, the misalignment of the appliance with the teeth will apply forces on the teeth at the points of contact. The larger the misalignment, the stronger the repositioning force. As the teeth gradually move into the desired configuration, the misalignment decreases and the applied force lessens. When the teeth substantially reach the desired configuration, the force may approach zero. It is at this point that the useful life of such an appliance for applying repositioning force has ended. The patient may then progress to the next stage in treatment plan and begin wearing the next successive elastic repositioning appliance. The new appliance will apply repositioning forces to move the teeth to the next desired configuration, repeating the appliance wear cycle.

Determining when to progress a patient to the next stage in a treatment plan is largely based on the discretion of the orthodontic practitioner. Gross misalignment of the appliance to the teeth of the patient may be evident by visual observation. However, as the teeth become more closely aligned with the appliance, the difference becomes less and less obvious. If a patient is advanced to the next stage in treatment prematurely, excessive forces may be applied to the teeth. Excessive force, in turn, may cause patient discomfort and possible biological consequences to the teeth and supporting tissue, such as undermining resorption. In addition, repeated premature progression may lead to poor fitting of the appliance and the application of undesired forces to the teeth. A poor fitting appliance may contact the teeth in unforeseen areas applying unprescribed forces to the teeth. The result may be undesired repositioning of the teeth.

Likewise, delay in progression to the next stage may unduly lengthen the treatment schedule, which may be unfavorable for both patient and practitioner. Lengthening of the treatment schedule may increase the possibility of treatment coinciding with other dental procedures, such as fillings, crowns, root canals, etc, which may interrupt the treatment plan. In addition, such lengthening may increase the possibility of tooth decay and/or periodontal disease in patients with poor dental hygiene.

Thus, it would be desired to provide dental appliances, systems and methods which may be used to more accurately assess and determine the useful life of such repositioning appliances. Such devices and methods should be economical, efficient and easy to use. In particular, they should provide indicators to assist in estimating the level of repositioning forces applied to the teeth when the appliance is placed over the teeth. At least some of these objectives, as well as others, will be met by the designs and methods of the present invention described hereinafter.

SUMMARY OF THE INVENTION

The present invention provides dental appliances, systems and methods which allow orthodontic practitioners to more easily monitor patient treatment progress. When using elastic repositioning appliances in orthodontic treatment, a patient may wear such an appliance until their teeth have repositioned to the tooth configuration prescribed by the appliance. At that point, the patient should progress to the next appliance for repositioning to the next tooth configuration in the treatment plan. Indications that the appliance is no longer supplying significant repositioning forces may be beneficial in the determination of progressing the patient to the next appliance or next stage in treatment. Mechanical stress in the material of the appliance, when the appliance is in place over the patient's teeth, may serve as an indicator of repositioning force applied against the teeth. Such stress may be visualized with the use of photoelastic material in or on the appliance.

Photoelasticity is the effect that causes a material to become "birefringent" when placed under stress. Birefringence may be described as the division of light into two components which is found in materials which have two different indices of refraction in different directions (i.e., when light entering certain transparent materials splits into two beams which travel at different speeds). The result is a fringe or interference pattern in the area under stress which may be observed in the presence of polarized light. Such patterns may be easily visually observed as an indication that the material is under mechanical stress.

In a first aspect of the present invention, a dental appliance comprises at least one layer of photoelastic material. In the case of an elastic repositioning appliance, the appliance comprises a shell having cavities shaped to receive teeth. The cavities may be misaligned with the patient's current tooth configuration such that placement of the appliance over the teeth will apply forces on the teeth at the points of contact. It may be appreciated that the appliance may also apply forces to the teeth through various attachment devices and similar accessories. In all cases, mechanical stress will occur in the material of the appliance in the areas where force is applied. The photoelastic material in the appliance is thus caused to become birefringent under such stress providing interference patterns which may allow identification of these areas by an observer, typically by simple visual observation.

In a second aspect of the present invention, a dental appliance comprising photoelastic material may be constructed in a variety of configurations. In one embodiment, the shell of an elastic repositioning appliance is created by thermal forming sheet of polymer material over a model or cast of the patient's teeth. Photoelastic material is also provided in a sheet form, and the photoelastic material is preferably thermal formed with the sheet of polymer to create the appliance. If the polymer material is itself photoelastic, the shell may be formed without the addition of a separate sheet of photoelastic material. Thus, the appliance may consist essentially of only a thermal formed sheet of photoelastic material, namely the polymer shell. In a further alternative embodiment, the photoelastic material may be applied to the appliance as a coating on the surface of the shell.

According to the methods of the present invention, all or portions of a dental appliance may be evaluated for the presence of mechanical stress as an indication of the progress of orthodontic treatment of a patient. As described above, a dental appliance comprises at least one layer of photoelastic material in at least a portion of the appliance. After the appliance is positioned over the teeth of a patient, polarized light is directed toward the designated area. Observation of interference patterns in the shell of the appliance (at least in the portion comprising the photoelastic material) indicates the presence of mechanical stress due to positioning of the appliance over the patient's teeth.

In a first aspect of the methods of the present invention, if mechanical stress is present, light will be refracted in a manner which forms an interference pattern. However, it may not be evident whether the stresses are due to the application of repositioning forces to the teeth or result from inherent stresses in the appliance. For instance, the material of the appliance may be under stress when the appliance is in a free state, i.e. when the appliance is removed from the patient's teeth and is not subjected to applied force. This may occur due to processing of the appliance or general wear on the appliance over time. For example, thermal forming of a photoelastic sheet may introduce permanent stresses into the walls of the appliance shell. Likewise, general use of the appliance may introduce plastic deformations in portions of the appliance forming permanent stresses in these areas. Therefore, the evaluation of interference pattern(s) in an appliance when placed over the patient's teeth may require further methods to determine if the stresses are due to the application of repositioning forces. Thus, the methods of the present invention further provide that polarized light may be directed toward the appliance while the appliance is in a free state. If it is observed that interference pattern(s) are not present in the free state, it may be concluded that the appearance of interference pattern(s) while the appliance is positioned over a patient's teeth are due to the continued application of repositioning forces and that the dental appliance is still useful in applying repositioning forces to the patient's teeth. If, on the other hand, it is observed that an interference pattern(s) are present in the free state, a comparison between the interference pattern(s) in the free state and the patterns(s) when the appliance is positioned over the patient's teeth should be made. If a change in the interference pattern is evident, it may be concluded that such a change is due to the application of repositioning forces. Therefore, it may be determined that the dental appliance is still useful in applying such forces.

In another aspect of the methods of the present invention, if mechanical stress is not present or is minimally present, light may be refracted in a manner which forms minimal or no interference pattern or an interference pattern which remains unchanged from the free state. Such observation indicates the absence of stress due to positioning of the appliance over the patient's teeth. Therefore, the dental appliance is likely no longer useful in applying repositioning forces.

In a fourth aspect of the methods of the present invention, the usefulness of an elastic repositioning appliance in applying repositioning forces to a patient's teeth may be monitored throughout orthodontic treatment. In a first embodiment, portions or all of a dental appliance may be evaluated as described above. Such methods may be repeated at predetermined intervals over time until absence of mechanical stress in the designated areas due to positioning of the appliance over the patient's teeth is observed. This will indicate that the patient's teeth have repositioned into the tooth arrangement prescribed by the appliance. Thus, at this point, the use of the appliance may be discontinued and replaced with another appliance having a different geometry selected to move the teeth to the next intermediate or final arrangement In a second embodiment, all or portions of a dental appliance may be evaluated as described above, and the intensity of the mechanical stress due to positioning of the appliance over the patient's teeth may be determined. This may be accomplished simply by noticing the size or specific characteristics of the interference pattern(s), or it may involve more detailed methods of photostress analysis. Such methods may be repeated at predetermined intervals over time until the intensity of the mechanical stress decreases to or below a threshold. This may indicate that the patient's teeth have sufficiently repositioned into the tooth arrangement prescribed by the appliance. Thus, at this point, the use of the appliance may be discontinued for repositioning purposes.

Other objects and advantages of the present invention will become apparent from the detailed description to follow, together with the accompanying drawings.

DESCRIPTION OF THE SPECIFIC EMBODIMENTS

Figure 1:
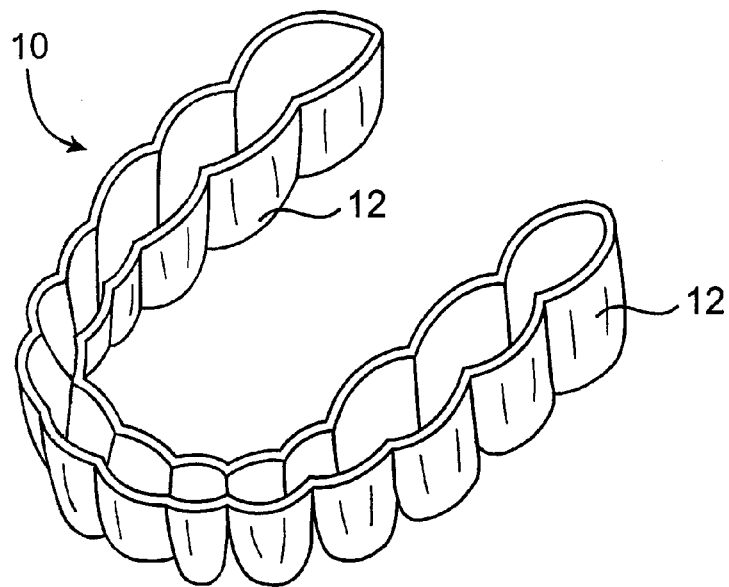
FIG. 1 illustrates an embodiment of an elastic repositioning appliance having a layer of photoelastic material.

When an appliance is placed over the teeth, the repositioning forces applied to the teeth may vary throughout the treatment period as the teeth are gradually repositioned. Since the repositioning forces are applied to the teeth by the polymeric walls of the appliance, an equal and opposite force will be applied to the walls of the appliance by the teeth. Such force against the polymeric material may be indicated and/or measured by stress within the material.

Thus, stress concentrations in the material of the appliance may be used as an indicator in the evaluation of applied repositioning forces by an appliance and therefore the useful life of such an appliance for a given patient.

A number of experimental techniques have been developed to determine and measure mechanical stresses in a material. One such technique which is particularly applicable to the present invention involves the use of photoelastic material. Photoelasticity may be described as changes in the optical properties of a transparent material when it is subjected to mechanical stress. Such changes may be termed birefringence, also known as mechanical birefringence or stress birefringence. Birefringence may be described as the resolution or splitting of a light wave into two waves with mutually perpendicular vibration directions by an optically anisotropic medium. The amount of component wave retardation is exhibited by fringes or interference patterns which express stress magnitude. Thus, photoelasticity is the effect that a material can become birefringent when placed under stress which provides interference patterns for identifying areas of stress. The effect is temporary as long as the elastic stress is not exceeded and it is in direct proportion to the applied load.

As described, when polarized light is passed through a stressed transparent photoelastic material, temporary double refraction, or birefringence, may be exhibited in the form of fringes or interference patterns. Ordinary white light or monochrome light may be used. White light is light of many different wavelengths combined which produces a colorful fringe pattern. Monochrome light is light of only one wavelength which produces black and white fringes. Fringes are similar to contour lines on a map; they represent a locus of points having the same difference in principle stresses. Such fringes or interference patterns may be used for a number of levels of analysis of material stresses. In relation to the present invention, it may only be necessary to observe the presence or absence of interference patterns at specific locations in the polymeric material of the appliance to determine if stresses are present. As the teeth are gradually repositioned, the stresses may reduce as may be reflected in diminishing interference patterns. It may be appreciated that baseline stresses may be present in the material of such an appliance which may be reflected in baseline interference patterns. In such a case, changes in the interference patterns may be used to determine induced stress rather than the mere presence of interference patterns.

Referring to FIG. 1, an elastic repositioning appliance 10 may be comprised of a layer of photoelastic material 12, depicted by shading. Photoelastic material is available in flat sheets, in a viscous form that can be molded or cast in the component geometry or in a liquid form for varnishing or coating the surface as by painting. Flat sheets may be utilized in the initial formation of the elastic repositioning appliance, comprising a shell having cavities to receive teeth. An overall method for producing elastic repositioning appliances is provided in U.S. Pat. No. 5,975,893, and in published PCT application WO 98/58596 which designates the United States and which is assigned to the assignee of the present application. But, in general, the shell is typically produced by heating a thermoformable polymer sheet and vacuum or pressure forming the sheet over the tooth members of a mold. Thus, the shell is a direct representation of the characteristics of the mold.

A flat sheet of photoelastic material may be adhered to or placed over a sheet of suitable elastomeric polymer, such as Tru-Tain thermal forming dental material (Tru-Tain Plastics, Rochester, Minn.), or Essix A-Type or Essix B-Type thermal forming material (Raintree-Essix, New Orleans, La.) prior to thermal forming. The result may be an elastic repositioning appliance having a layer of photoelastic material on its outside surface as depicted in FIG. 1. It may be appreciated that such a layer may also be located on the inside surface, on both surfaces or in selected areas on either surface. Also, such a layer may be embedded within such an appliance, as in the case of a layer of photoelastic material sandwiched between sheets of thermal forming dental material. Alternatively, the thermal forming material may itself have photoelastic properties in which case the thermal forming material may be considered a photoelastic material. Thus, additional layers of photoelastic material may not be necessary.

Photoelastic material may also be applied to the formed polymeric shell of an elastic repositioning appliance. Such material may be molded or cast on the shell to form a surface layer. Such a layer may be on the outside surface of the shell, as depicted in FIG. 1, on the inside surface, on both surfaces or in selected areas on either surface. Likewise, such photoelastic material may be painted on or applied to the surface of the shell as a varnish or coating. Again, such a layer may be on the outside surface of the shell, as depicted in FIG. 1, on the inside surface, on both surfaces or in selected areas on either surface.

Figure 2:
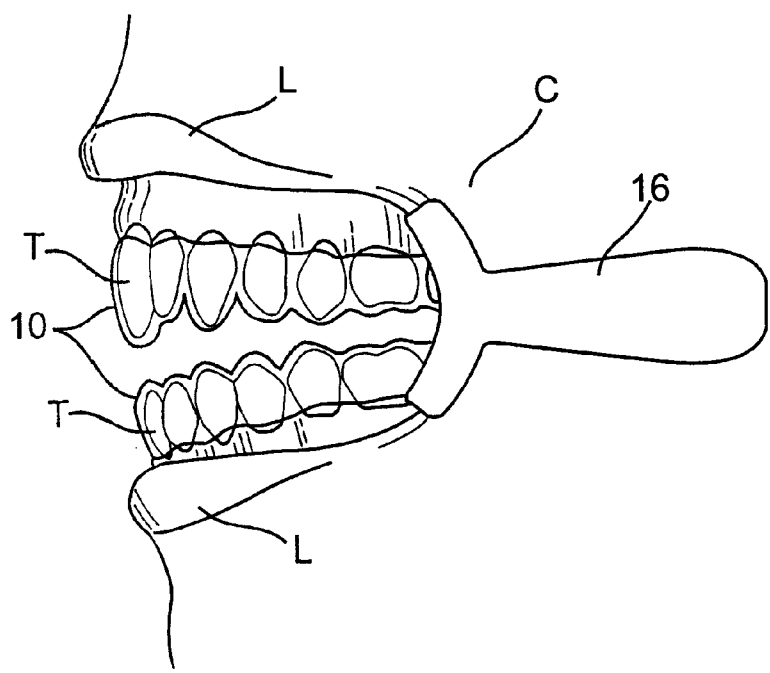
FIG. 2 depicts an appliance of FIG. 1 positioned over the teeth of patient with lips and cheek retracted for evaluation of the appliance.

Referring to FIG. 2, the elastic repositioning appliance 10 may be placed over the patient's teeth T for evaluation of the presence of mechanical stress. Since birefringence involves the splitting of light waves, the portion of the appliance 10 under observation must be exposed to light both for the effect of birefringence and for the observation of such effects. This may involve simply opening the patient's jaws and/or pulling the lips L and cheeks C away from the teeth T. As shown in FIG. 2, such maneuvers may be aided by the use of a retraction instrument 16.

Figure 3:
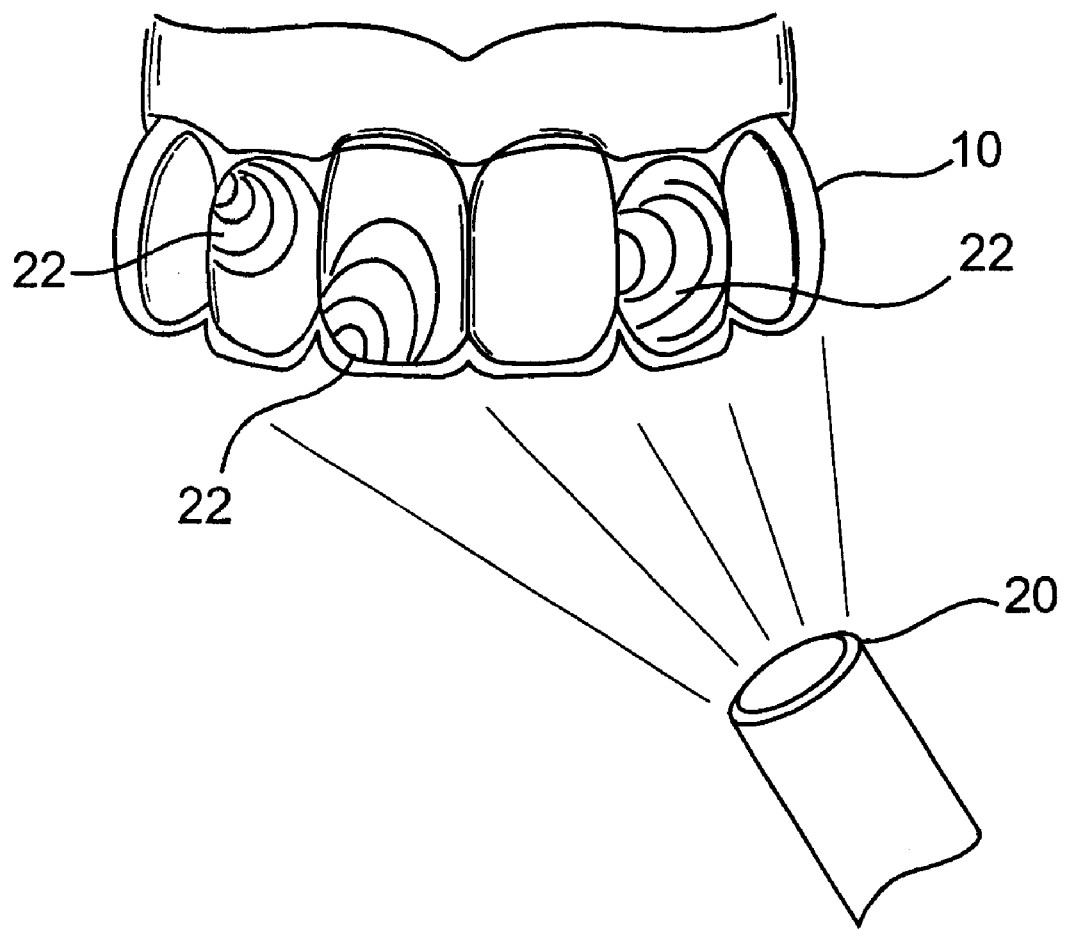
FIG. 3 illustrates the presence of interference patterns in an appliance when polarized light is aimed thereon.

Referring to FIG. 3, a polarized light source 20 may be aimed at a portion of the elastic repositioning appliance 10 for stress evaluation. The light source 20 may be contained in a hand-held probe or wand, mounted on a standard overhead examination light, or housed in any suitable apparatus. When the portion of the appliance 10 is viewed using polarized light, fringes or interference patterns 22 may be easily located and distinguished. As previously stated, it may only be necessary to observe the presence or absence of interference patterns 22 in the polymeric material of the appliance to determine if stresses are present. When the teeth T are generally aligned with the tooth receiving cavities of the polymeric shell, stresses may be minimal or non-existent leading to the absence of interference patterns 22. This may particularly be the case when the photoelastic material is coated or layered on the appliance 10 after the appliance has been thermal formed into the appropriate shape. Here the photoelastic material may have a minimal or nonexistent baseline stress, i.e. prior to placement over the patient's teeth. Alternatively, as may particularly be the case when the photoelastic material is thermal formed into the appropriate shape for the appliance, baseline stresses may be present in the material of the appliance before it is placed over the patient's teeth. In this case, changes in the interference patterns 22 may be used to determine induced stress rather than the mere presence of interference patterns 22.

Interference patterns 22 which suggest the presence of mechanical stress in the appliance 10 may be used by the orthodontic practitioner as an indicator in determining the progress of a patient during treatment. At predetermined intervals throughout a given treatment phase, a practitioner may examine the optical properties of a given repositioning appliance placed over the patient's teeth. Generally, as the patient's teeth reposition to more closely reflect the tooth arrangement prescribed by the repositioning appliance, the intensity of the mechanical stresses decrease. This may be seen as diminishments in the interference patterns 22 or changes in the patterns 22 to more closely reflect baseline patterns. A threshold may be established, at or below which the practitioner may consider the useful life oft he appliance to have been reached for repositioning purposes. At that time, the patient may progress to the next stage in treatment. If it is desired to reposition the teeth further, a new appliance may be prescribed with a new tooth configuration. Such a new appliance may be comprised of photoelastic material as described above for similar monitoring and indication purposes.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A method of detecting stress in a dental appliance when placed over teeth, said method comprising:

providing a dental appliance comprising at least one layer of photoelastic material;

positioning the appliance over a patient's teeth;

directing polarized light toward the photoelastic material while the appliance is over the patient's teeth;

observing the extent of interference patterns in the photoelastic material in the presence of polarized light.

2. A method of claim 1, further comprising:

directing polarized light toward the photoelastic material while the appliance is in a free state; and observing the photoelastic material while the appliance is in the free state as a baseline for comparison when the appliance placed over teeth.

3. A method of claim 2, further comprising comparing the baseline with the interference patterns observable while the shell is in place over the teeth.

4. A method of claim 1, wherein the absence of an interference pattern indicates the absence of stress due to positioning of the appliance over the patient's teeth.

5. A method as in claim 1, wherein the presence of an interference pattern indicates the presence of stress due to positioning of the appliance over the patient's teeth.

6. A method of claim 1, further comprising providing the patient with a new appliance when it has been determined that the appliance is no longer under significant stress.

7. A method of monitoring usefulness of an elastic repositioning appliance in applying repositioning forces to a patient's teeth during orthodontic treatment, said method comprising:

providing a dental appliance comprising at least one layer of photoelastic material;

positioning the appliance over a patient's teeth;

directing polarized light toward the photoelastic material while the appliance is over the patient's teeth;

observing the extent of interference patterns in the photoelastic material in the presence of polarized light;

repeating the evaluation at predetermined intervals over time until absence of mechanical stress in the designated areas due to positioning of the appliance over the patient's teeth is observed; and discontinuing use of the appliance for repositioning purposes when said absence is observed.

8. A method of claim 7, further comprising replacing the appliance with another appliance.

9. A method of monitoring usefulness of an elastic repositioning appliance in applying repositioning forces to a patient's teeth during orthodontic treatment, said method comprising:

providing a dental appliance comprising at least one layer of photoelastic material;

positioning the appliance over a patient's teeth;

directing polarized light toward the photoelastic material while the appliance is over the patient's teeth;

observing the extent of interference patterns in the photoelastic material in the presence of polarized light;

repeating the evaluation at predetermined intervals over time until the extent of the mechanical stress decreases to or below a threshold; and discontinuing use of the appliance for repositioning purposes when said threshold is reached.

10. A method of claim 9, further comprising replacing the appliance with another appliance.

11. A dental appliance comprising:

an elastic shell having cavities shaped to receive and move teeth, said shell comprising at least one layer of photoelastic material.

12. A dental appliance of claim 11, wherein the photoelastic material becomes birefringent under mechanical stress providing visually observable interference patterns for use in identifying areas under said stress.

13. A dental appliance of claim 12, wherein the layer of photoelastic material is oriented so that when the shell is positioned over teeth the mechanical stress results from placing the shell over the teeth and will be observable while the shell is in place over the teeth.

14. A dental appliance of claim 11, wherein the shell comprises a base polymer layer attached to the layer of photoelastic material.

15. A dental appliance as in claim 14, wherein the layers have been thermally formed together into the shell.

16. A dental appliance of claim 11, wherein the shell consists essentially of a thermal formed sheet of photoelastic material.

17. A dental appliance of claim 11, wherein the layer of photoelastic material comprises a coating applied over a surface of the shell.

* * * * *